United States Patent
Maschke

(10) Patent No.: US 7,637,885 B2
(45) Date of Patent: Dec. 29, 2009

(54) CATHETER DEVICE FOR APPLYING A MEDICAL CUTTING BALLOON INTERVENTION

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 329 days.

(21) Appl. No.: 11/092,790

(22) Filed: Mar. 29, 2005

(65) Prior Publication Data
US 2005/0222594 A1    Oct. 6, 2005

(30) Foreign Application Priority Data
Mar. 31, 2004  (DE) .................. 10 2004 015 640

(51) Int. Cl.
*A61M 29/00* (2006.01)
(52) U.S. Cl. .................................................. 604/96.01
(58) Field of Classification Search ................. 600/470, 600/466, 467; 604/22, 96.01; 606/159, 191, 606/194; 623/1.1
See application file for complete search history.

(56) References Cited

U.S. PATENT DOCUMENTS

| | | | | |
|---|---|---|---|---|
| 4,465,072 A | * | 8/1984 | Taheri | 606/159 |
| 4,603,699 A | * | 8/1986 | Himpens | 600/486 |
| 4,646,742 A | * | 3/1987 | Packard et al. | 606/194 |
| 4,909,252 A | * | 3/1990 | Goldberger | 606/194 |
| 5,049,124 A | * | 9/1991 | Bales, Jr. | 604/22 |
| 5,193,546 A | | 3/1993 | Shaknovich | |
| 5,196,024 A | * | 3/1993 | Barath | 606/159 |
| 5,549,551 A | * | 8/1996 | Peacock et al. | 604/103.05 |
| 5,699,805 A | * | 12/1997 | Seward et al. | 600/459 |
| 5,741,270 A | * | 4/1998 | Hansen et al. | 606/108 |
| 5,872,879 A | * | 2/1999 | Hamm | 385/25 |
| 5,906,579 A | * | 5/1999 | Vander Salm et al. | 600/424 |
| 5,921,926 A | | 7/1999 | Rolland et al. | |
| 6,010,449 A | * | 1/2000 | Selmon et al. | 600/117 |
| 6,258,052 B1 | | 7/2001 | Milo | |
| 6,497,711 B1 | | 12/2002 | Plaia et al. | |
| 6,608,684 B1 | * | 8/2003 | Gelikonov et al. | 356/479 |
| 6,623,496 B2 | * | 9/2003 | Snow et al. | 606/159 |
| 2002/0019644 A1 | | 2/2002 | Hastings et al. | |
| 2002/0077647 A1 | | 6/2002 | Snow et al. | |
| 2003/0125630 A1 | * | 7/2003 | Furnish | 600/461 |

FOREIGN PATENT DOCUMENTS

| | | |
|---|---|---|
| EP | 0 815 801 B1 | 1/1998 |
| EP | 0 885 594 B1 | 12/1998 |
| WO | WO 82/04388 | 12/1982 |
| WO | WO 01/11409 A2 | 2/2001 |
| WO | WO 02/078511 A2 | 10/2002 |

OTHER PUBLICATIONS

Cutting Balloon Ultra[2]™ Over the Wire Device, Boston Scientific Corporation, [retrieved on Mar. 29, 2005], Retrieved from [online], http://www.bostonscientific.com/med_ specialty/deviceCategoryList.jhtml?task=tskCategoryList.jhtml&sectionId=4 &relId=2,74,11005.

(Continued)

*Primary Examiner*—Darwin P Erezo
*Assistant Examiner*—Gregory Anderson

(57) ABSTRACT

Device for carrying out a cutting balloon intervention using a cutting balloon catheter with an inflatable balloon arranged in the region of its front end holding an axially positioned blade and with OCT monitoring, the cutting balloon catheter being combined with an OCT catheter to form an integrated unit.

7 Claims, 2 Drawing Sheets

OTHER PUBLICATIONS

Cutting Balloon Ultra²™ Monorail® Device, Boston Scientific Corporation, [retrieved on Mar. 29, 2005], Retrieved from [online], http://www.bostonscientific.com/med_specialty/deviceCategoryList.jhtml?task=tskCategoryList.jhtml&sectionId=4&relId=2,74,11005.

Nakamura, Mamoo et al., "Impact of Deep Vessel Wall Injury on Acute Response and Remodeling of Coronary Artery Segments After Cutting Balloon Angioplasty", The American Journal of Cardiology, Jan. 1, 2003, pp. 6-11, vol. 91.

Peter Barath, Michael C. Fishbein, Sandor Vari and James S. Forrester, "Cutting Balloon: A Novel Approach to Percutaneous Angioplasty", The American Journal of Cardiology, Nov. 1, 1991, pp. 1249-1252, vol. 68.

* cited by examiner

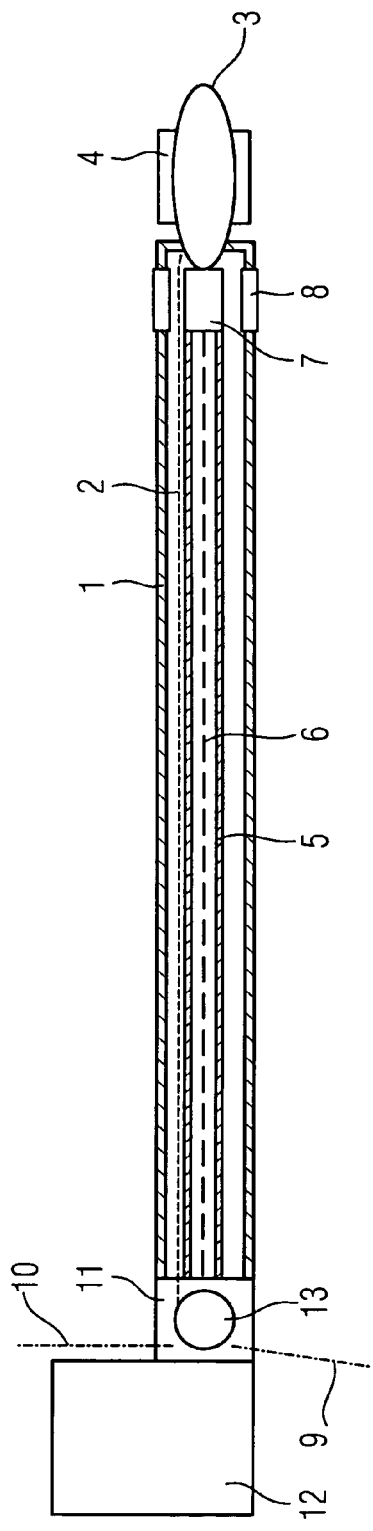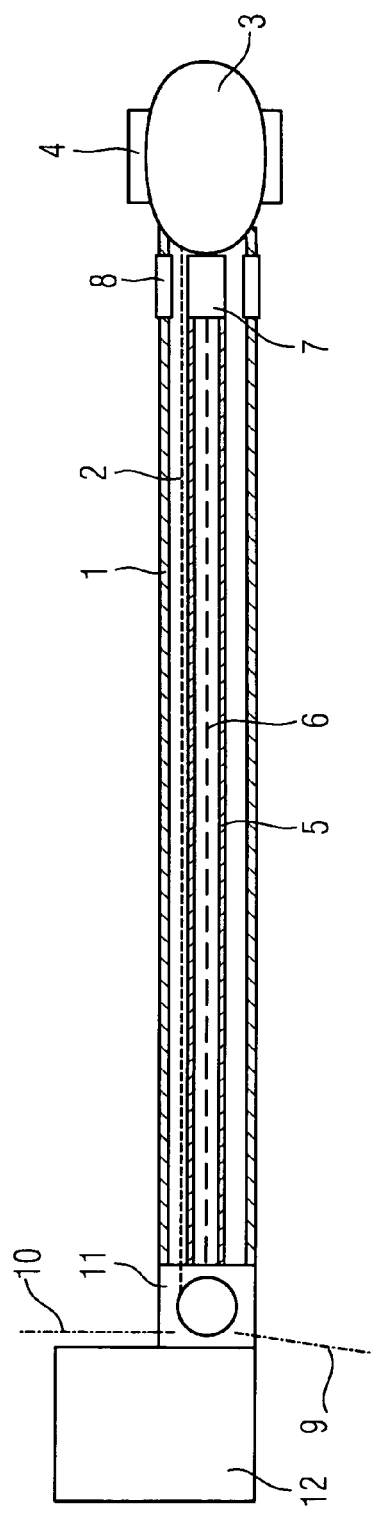

CATHETER DEVICE FOR APPLYING A MEDICAL CUTTING BALLOON INTERVENTION

CROSS REFERENCE TO RELATED APPLICATIONS

This application claims priority to the German application No. 10 2004 015 640.9, filed Mar. 31, 2004 which is incorporated by reference herein in its entirety.

FIELD OF INVENTION

The invention relates to a device for carrying out a cutting balloon intervention using a cutting balloon catheter with an inflatable balloon arranged in the region of its front end holding axially positioned blades and with OCT monitoring.

BACKGROUND OF INVENTION

Among the most common fatal diseases are vascular diseases, in particular cardiac infarction. This is caused by disease of the coronary vessels (atherosclerosis). Deposits (atherosclerotic plaque) thereby cause a blockage of the coronary vessels.

If coronary angiography shows severe restriction (stenosis) in the coronary vessels, which causes angina pectoris, restricts performance and/or threatens the life of the patient, in the majority of cases today a PTCA (Percutaneous Transluminal Coronary Angioplasty) is carried out. To this end the restrictions in the coronary vessels are dilated with the so-called balloon catheter.

The action mechanism of conventional balloon angioplasty for lumen gain is based on the one hand on compression of the plaque and on the other hand on rearrangement of the non-compressible plaque, components by dissection of the vessel intima and media and over-dilation of the circumference of the vessel. Compression of large quantities of plaque can result in damage to the inner wall of the vessel, which leads to an increase in the restenosis rate.

The use of a stent in the expanded segment of the vessel can reduce the restenosis rate. Stent implantation prevents structural changes in the vessel due to the mechanical restoring force of the stent. A clear disadvantage of the method is the additional process step and the additional cost of the stent.

The cutting balloon is a special balloon holding three or four small blades depending on size. When the balloon opens, these become aligned and make longitudinal cuts in the vessel deposits or "shave" plaque from the vessel wall, before the coronary artery is dilated by the balloon.

The object of this technique is to reduce or even eliminate the elastic restoring forces, to achieve a larger vessel diameter after dilation. It also prevents irregular tearing of the vessel intima, which could be responsible for acute occlusions after balloon dilation. Studies show that hyperplasia (inflammation response with swelling) of the intima can be reduced after balloon dilation and the restenosis rate is thus significantly reduced by use of the cutting balloon.

A device according to the cutting balloon principle is for example disclosed in WO 82/04388, "Coronary Cutting and Dilating Instrument" and in WO 02/078511 "Inflatable Medical Device with Combination Cutting Elements and Drug Delivery Conduits". A known product is for example the Cutting Balloon Ultra from Boston Scientific, MA, USA.

The intervention described above is carried out subject to X-ray control using contrast agents with an angiograph device. The disadvantage of this method is that the coronary vessels are only displayed as two-dimensional and only the actual constriction is shown in the X-ray image. During the intervention it is difficult for medical personnel to distinguish between plaque and vascular wall. This increases the risk that the blades of the balloon might cut in the wrong place or the cuts might be too deep (deep vessel wall injury).

The problem is described for example in the document "Impact of Deep Vessel Injury on Acute Response and Remodeling of Coronary Artery Segments After Cutting Balloon Angioplasty", Mamoo Nakamura, The American Journal of Cardiology Vol. 91, Jan. 1, 2003.

Insertion of an IVUS catheter (Intravascular Ultrasound) into the vessel improves the imaging information but has the disadvantage that a relatively expensive catheter also has to be inserted into the patient and must be removed from the vessel before insertion of the balloon catheter. An IVUS system is for example disclosed in EP 0 885 594 B1 and in U.S. Pat. No. 5,193,546. The disadvantage of the IVUS solution is the limited spatial resolution of the ultrasound method.

Significantly better spatial resolution, in particular in the relevant close-up range, could be provided by an OCT catheter, which is inserted separately into the vessel.

The OCT method is for example disclosed in WO 01/11409 A2, in U.S. Pat. No. 5,921,926 and in EP 0 815 801 B1. The OCT technique operates in a similar fashion to imaging ultrasound (B mode). The essential physical principle is based on the Michelson interferometer.

The disadvantage of this method is that the OCT device has to be withdrawn from the vessel whenever the cutting balloon is inserted.

SUMMARY OF THE INVENTION

An object of the invention is therefore to configure a device of the type mentioned above such that an optimal, easy to operate device is provided, with which the intervention site can be directly observed, if necessary even as the vessel is being extended, without complex swapping of the various catheters.

This object is achieved by the claims.

The configuration according to the invention results in an integrated unit comprising a cutting balloon catheter with an OCT catheter integrated therein, which represents an optimum system for opening up total vascular stenoses. The major advantage of the solution is the reduction in the number of method steps and the reduction in the number of catheters used, as well as the reduction in exposure to X-ray radiation. The images of the OCT system provide important additional medical information with a high resolution, in particular in the close-up range, about the plaque and the vascular wall. The plaque can thereby be identified in each instance and the plaque can be removed from the correct sites using the cutting balloon.

According to a first embodiment of the present invention, rotating OCT lines can be arranged in the tubular sheath of the cutting balloon catheter in addition to the inflation line for the balloon, said OCT lines running to an OCT sensor arranged inside a circumferential annular window in the catheter sheath directly behind the cutting balloon.

As an alternative to this embodiment the configuration can also be such that rotating OCT lines are arranged in the tubular sheath of the cutting balloon catheters in addition to the inflation line for the balloon, said OCT lines running to a [lacuna] directly in front of the OCT sensor configured as an annular balloon to implement the OCT signal lines.

With both embodiments it has proven particularly expedient for the configuration to be such that the OCT signal line, preferably configured as a glass-fiber line, runs inside a hollow flexible drive shaft for the OCT sensor.

With the embodiment with OCT sensor arranged in the front position, to ensure unimpeded rotation of its drive shaft inside the cutting balloon configured as an annular balloon, according to a further feature of the present invention the catheter sheath can have a tapered rigid section holding the cutting balloon, in which section the hollow flexible drive shaft for the OCT sensor arranged in the front position is contained.

It has also proven expedient with this embodiment for the OCT sensor not to be exposed at the front end of its drive shaft but to be arranged inside a circumferential annular window of the hollow flexible drive shaft.

According to a further feature of the present invention the OCT catheter sheath should be provided with inlet and outlet openings at its ends for a contrast agent or a rinsing fluid, so that the intervention area to be observed in each instance can be rinsed clean, thereby allowing better observation.

In addition to magnets that can be arranged in the region of the tip of the cutting balloon catheter for magnetic navigation in the vessel, there can optionally also be provision for a preferably multi-chamber, inflatable balloon to be arranged at the tip of the cutting balloon catheter to hold the catheter in the vessel and/or to dilate the vessel.

Finally it is also within the scope of the invention that the device has a guide wire or guide catheter running through it.

A typical method sequence when using a device according to the invention is as follows:

Insertion of a guide wire or guide catheter subject to X-ray control, in some instances with contrast agent, into the target position (stenosis).

Insertion of the integrated cutting balloon catheter subject to X-ray control, in some instance with contrast agent, into the target position.

Once in the required target position the rinsing fluid for the OCT method is injected and the site from which the plaque is to be removed is observed at high resolution.

The cutting balloon intervention is then carried out gradually in the plaque, with the option of verifying progress using OCT after each dilation process.

Once the full intervention has been completed, the complete vessel segment is checked once again with OCT.

In addition to the combined cutting balloon-OCT catheter discussed above, the device according to the invention also has a unit to link the proposed catheter to a user interface for the part of the integrated catheter used to remove the plaque. In addition to a signal interface unit and a preprocessing stage for the OCT image data, an image processing and image display unit is provided with an image storage unit. A power supply unit and network interface are of course also present.

The OCT image system can be extended to include menus to allow quantification of the stenosis to be removed, for example the extent of the stenosis before and after intervention. The user interface can also have input options so that patient data and data for the catheter parameters can be input using a keyboard and/or barcode or a mouse.

BRIEF DESCRIPTION OF THE DRAWINGS

Further advantages, features and details of the invention will emerge from the description which follows of some exemplary embodiments and with reference to the drawing, in which:

FIG. 1 shows a schematic diagram of the structure of a combined cutting balloon-OCT catheter according to the invention with an OCT sensor arranged directly behind the balloon, with the cutting balloon in the uninflated insertion stage, FIG. 2 shows a view corresponding to FIG. 1 after inflation of the cutting balloon.

DETAILED DESCRIPTION OF INVENTION

Figure 3:
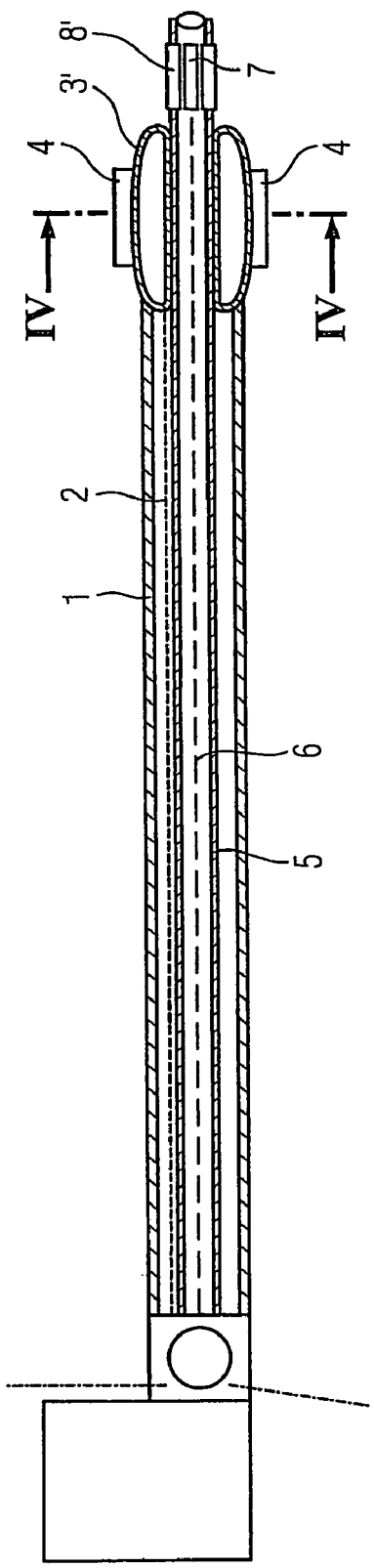
FIG. 3 shows a modified embodiment of the arrangement according to FIG. 1 with the OCT sensor arranged in front of the cutting balloon.

FIGS. 1 and 2 show schematic diagrams of the basic structure and operating mode of the cutting balloon catheter with integrated OCT monitoring according to the invention to be used for stenosis removal. Arranged inside the flexible catheter sheath 1 is an inflation line 2 to inflate the cutting balloon 3 fixed at the front end of the catheter sheath 1, on the outside of which cutting balloon there are a plurality of in particular three to four cutting blades 4, arranged with their axes essentially parallel. When the balloon opens, these blades 4 make longitudinal cuts in the vascular deposits or "shave" plaque from the vessel wall, before the coronary artery is dilated by the balloon.

A hollow flexible drive shaft 5 with a glass-fiber signal line 6 arranged therein for an OCT sensor 7 preferably configured as a mirror, which is arranged directly behind the cutting balloon 3 inside a transparent annular window 8 in the catheter sheath 1, is arranged in the flexible catheter sheath 1 in addition to the inflation line 2. A link for contrast agents and rinsing fluid, which can be pumped through the catheter sheath 1 to an outlet opening (not shown) arranged in the region of the annular window 8 is shown as 9. 10 shows the connecting line for the supply of pressurized gas or pressurized fluid to the inflation line 2 for the cutting balloon.

The combined cutting balloon-OCT catheter is connected via the mechanical connecting system 11 to the signal interface and the drive unit 12 for the OCT system. This mechanical connecting system 11 thereby contains a rotary coupling 13 for the links.

Once the balloon has been moved to the intervention site in the vessel it is inflated from the insertion position according to FIG. 1 to the position according to FIG. 2 by feeding in the pressure medium via the line 10 and the inflation line 2, longitudinal cuts first being made by the cutting blades 4 in the vessel deposits, before the vessel, in particular a coronary artery, is expanded by the inflating balloon, so that the plaque breaks off.

Figure 4:
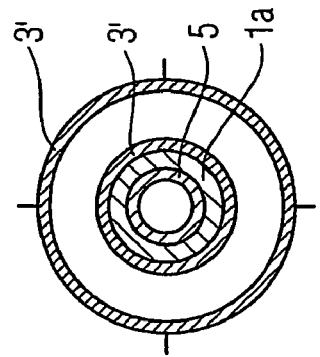
FIG. 4 shows a section along the line IV-IV in FIG. 3.

In the modified exemplary embodiment shown in FIGS. 3 and 4 the OCT sensor 7 is arranged in front of the cutting balloon 3' configured here as an annular balloon, in other words the hollow flexible drive shaft 5 for the OCT sensor 7 with the OCT signal line 6 arranged therein runs through the annular balloon, which is fixed to the catheter sheath 1 as before. With the embodiment shown the OCT sensor is thereby located inside an annular window 8' in the hollow flexible drive shaft 5.

Figure 5:
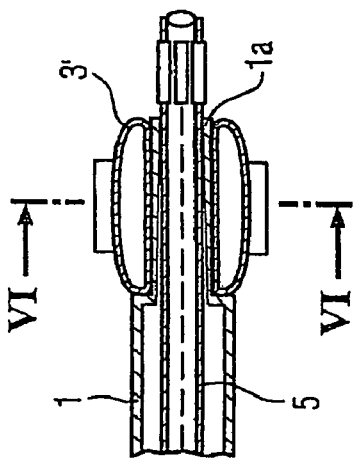
FIG. 5 shows the front end of an embodiment modified even further compared with FIG. 3, with a tapered support end of the catheter sheath holding the cutting balloon configured as an annular balloon
Figure 6:
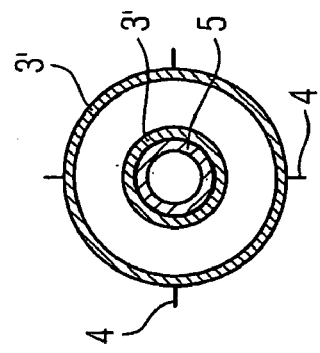
FIG. 6 shows a section VI-VI in FIG. 5.

To achieve less impeded rotation of the drive shaft 5 for the OCT sensor running through this cutting balloon 3' compared with this embodiment according to FIGS. 3 and 4, with the exemplary embodiment according to FIGS. 5 and 6 the cutting balloon 3' is not simply arranged freely at the front end of the catheter sheath 1 but is supported on a tapered, rigid section running through the cutting balloon 3', in which the hollow flexible drive shaft 5 for the OCT sensor 7 arranged in front is in turn supported in a sliding manner. This means that the drive shaft 5 does not slide with correspondingly high friction against the inner wall of the annular cutting balloon 3' but against the rigid section 1*a*, configured to be low friction, of the catheter sheath 1, which cannot also be pressed against the drive shaft 5 by the inflation pressure of the cutting balloon as it was in the previous exemplary embodiment.

The invention is not restricted to the exemplary embodiments shown. Magnetic navigation would therefore also be possible, with permanent magnets or alternatively electromagnets on the catheter tip or on the catheter, said magnets and their positions not being shown in the figures. An inflatable balloon, preferably even with a plurality of chambers, could also be arranged in the region of the tip, to position or hold the catheter tip in the required position during the intervention and also to be deployed as a dilation balloon if required. This balloon is not shown in the drawings either. Also X-ray markers known per se could be provided on the catheter shaft and also of course openings for a guide wire. Finally it should be noted that the proposed solution of a combined cutting balloon-OCT catheter for removing total stenoses is not restricted to use in coronary vessels but is essentially suitable for all types of vessels in the body.

The invention claimed is:

1. A catheter device for applying a medical cutting balloon intervention to a patient, comprising:
    a cutting balloon catheter having an inflatable balloon arranged at a catheter tip of the balloon catheter, the balloon catheter comprising a blade arranged along a longitudinal axis of the balloon catheter;
    a catheter jacket formed as a tube for accommodating the balloon catheter, the catheter jacket comprising a tapered and rigid section that supports the inflatable balloon;
    an OCT catheter for monitoring the medical cutting balloon intervention;
    a rotating OCT signal line for transmitting OCT signals wherein the balloon catheter and OCT catheter form one integrated unit; and
    an inflation line for inflating the balloon, wherein the rotating OCT signaling line is connected to an OCT sensor arranged upstream the balloon relative to the catheter tip, the balloon is configured as a ring-shaped balloon, the inflation line and the OCT signaling line are arranged within the catheter jacket, and the OCT signaling line is guided through a central opening of the ring shaped balloon;
    wherein the OCT signaling line is arranged within a hollow and flexible drive shaft for driving the OCT sensor and wherein the hollow and flexible drive shaft is arranged within the tapered and rigid section of the catheter jacket, the tapered and rigid section forming a sliding support for the hollow and flexible drive shaft, and wherein the OCT sensor is arranged behind a circular ring-shaped window of the hollow flexible drive shaft.

2. The device according to claim 1, wherein the OCT signaling line comprises an optical fiber.

3. The device according claim 1, wherein the catheter jacket comprises inlet and outlet openings for feeding and respectively discharging from the balloon catheter a contrast medium or a rinsing fluid.

4. The device according to claim 1, further comprising a plurality of magnets arranged at the catheter tip for enabling a magnetic navigation of the device.

5. The device according to claim 1, further comprising a further inflatable balloon arranged at the catheter tip for fixing a position of the balloon catheter within a vessel or for vessel dilatation.

6. The device according to claim 5, wherein the further inflatable balloon comprises a plurality of inflatable chambers.

7. The device according to claim 1, further comprising a continuous guide wire or a continuous guide catheter.

* * * * *